(12) United States Patent
Yang et al.

(10) Patent No.: US 11,738,183 B2
(45) Date of Patent: Aug. 29, 2023

(54) MEDICAL BALLOON HAVING A PLURALITY OF STRUCTURAL LAYERS

(71) Applicant: Covidien LP, Mansfield, MA (US)

(72) Inventors: Kumin Yang, Plymouth, MN (US); Frederick Feller, Maple Grove, MN (US)

(73) Assignee: COVIDIEN LP, Mansfield, MA (US)

( * ) Notice: Subject to any disclaimer, the term of this patent is extended or adjusted under 35 U.S.C. 154(b) by 850 days.

(21) Appl. No.: 16/750,822

(22) Filed: Jan. 23, 2020

(65) Prior Publication Data

US 2020/0155818 A1    May 21, 2020

Related U.S. Application Data

(63) Continuation of application No. 15/668,410, filed on Aug. 3, 2017, now Pat. No. 10,576,254.

(60) Provisional application No. 62/371,285, filed on Aug. 5, 2016.

(51) Int. Cl.
| | |
|---|---|
| *A61M 25/10* | (2013.01) |
| *A61M 25/00* | (2006.01) |
| *A61L 29/14* | (2006.01) |
| *A61L 29/12* | (2006.01) |

(52) U.S. Cl.
CPC ....... *A61M 25/1029* (2013.01); *A61L 29/126* (2013.01); *A61L 29/143* (2013.01); *A61M 25/0012* (2013.01); *A61M 25/10* (2013.01); *A61L 2400/10* (2013.01); *A61M 2025/0056* (2013.01); *A61M 2025/105* (2013.01); *A61M 2025/1075* (2013.01); *A61M 2025/1084* (2013.01)

(58) Field of Classification Search
CPC .. A61L 29/143; A61L 2400/10; A61L 29/126; A61M 2025/0056; A61M 2025/1084; A61M 25/0012; A61M 25/1029; A61M 2025/105; A61M 2025/1075; A61M 25/10
See application file for complete search history.

(56) References Cited

U.S. PATENT DOCUMENTS

| | | |
|---|---|---|
| 4,723,549 A | 2/1988 | Wholey et al. |
| 4,896,669 A | 1/1990 | Bhate et al. |
| 5,201,706 A | 4/1993 | Noguchi et al. |
| 5,447,497 A | 9/1995 | Sogard |
| 5,512,051 A | 4/1996 | Wang et al. |
| 5,587,125 A | 12/1996 | Roychowdhury |
| 5,868,779 A | 2/1999 | Ruiz |
| 5,972,019 A | 10/1999 | Engelson et al. |

(Continued)

FOREIGN PATENT DOCUMENTS

WO    2007123588    11/2007

OTHER PUBLICATIONS

Feeley, Dominic, "Advanced Coextruded Multilayer Tubing Allows Smaller, Thinner, More Functional Catheter-Based Devices", Brochure, www.ventionmedical.com, 2015, 8pgs.

*Primary Examiner* — Jason E Flick
(74) *Attorney, Agent, or Firm* — Stinson LLP (57) ABSTRACT

A plurality of structural layers having different properties are nested together to form the medical balloon. Certain embodiments include at least one layer comprising a fiber-reinforced polymer. The layers of the balloons can slide relative to one another in use. A structural layer may comprise metal reinforcing fibers suspended in a polymer matrix.

14 Claims, 7 Drawing Sheets

(56) References Cited

U.S. PATENT DOCUMENTS

| | | |
|---|---|---|
| 6,156,254 A | 12/2000 | Andrews et al. |
| 6,626,861 B1 | 9/2003 | Hart et al. |
| 8,568,648 B2 | 10/2013 | Stupecky et al. |
| 8,672,990 B2 | 3/2014 | Holman et al. |
| 8,900,215 B2 | 12/2014 | Pepper et al. |
| 9,114,236 B2 | 8/2015 | Davies, Jr. et al. |
| 9,180,620 B2 | 11/2015 | Devens, Jr. |
| 9,211,391 B2 | 12/2015 | Davies, Jr. et al. |
| 2005/0015046 A1 | 1/2005 | Weber |
| 2006/0085023 A1 | 4/2006 | Davies et al. |
| 2007/0265565 A1 | 11/2007 | Johnson |
| 2008/0033477 A1 | 2/2008 | Campbell |
| 2009/0301643 A1* | 12/2009 | Tilson ................ A61B 17/8827 156/212 |
| 2018/0002929 A1 | 1/2018 | Gandhi |

\* cited by examiner

MEDICAL BALLOON HAVING A PLURALITY OF STRUCTURAL LAYERS

CROSS-REFERENCE TO RELATED APPLICATION

The present application is a continuation of U.S. patent application Ser. No. 15/668,410, filed Aug. 3, 2017, which claims the benefit of U.S. Provisional Ser. No. 62/371,285, filed Aug. 5, 2016, the entirety of each of which is hereby incorporated by reference.

FIELD OF THE DISCLOSURE

The present disclosure generally relates to a medical balloon, such as non-compliant or semi-compliant medical balloons having multiple structural layers.

BACKGROUND OF THE DISCLOSURE

Balloons mounted on the distal ends of catheters are widely used in medical treatment. The balloon may be used to widen a vessel into which the catheter is inserted, open a blocked vessel and/or deliver a medical device to a body location, among other uses. The medical balloon includes a central body section, which is typically tubular, opposite cone sections at opposite longitudinal ends of the body section, and opposite waist sections at opposite longitudinal ends of the balloon. In use, the uninflated balloon is delivered to a treatment location within a body lumen (e.g., a blood vessel) by tracking through an introducer sheath and exiting a distal end of the sheath to reach the treatment location. Once the uninflated balloon has reached the treatment location, fluid is delivered into the balloon, thereby expanding the outer circumference of the balloon (i.e., the balloon is inflated). After treatment, the balloon is deflated and "pulled back" into the introducer sheath. The balloon catheter can then be withdrawn from the introducer sheath and the patient's body. It may be necessary or desired to re-introduce the balloon catheter into a body lumen, through the introducer sheath, to further treat the body lumen.

SUMMARY OF THE DISCLOSURE

In one aspect, a plurality of structural layers having different properties are nested together to form the medical balloon. Certain embodiments include at least one layer comprising a fiber-reinforced polymer. In one or more embodiments, the layers of the balloons can slide relative to one another in use.

In another aspect, a medical balloon structural layer comprises metal reinforcing fibers suspended in a polymer matrix.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE DISCLOSURE

Figure 1:
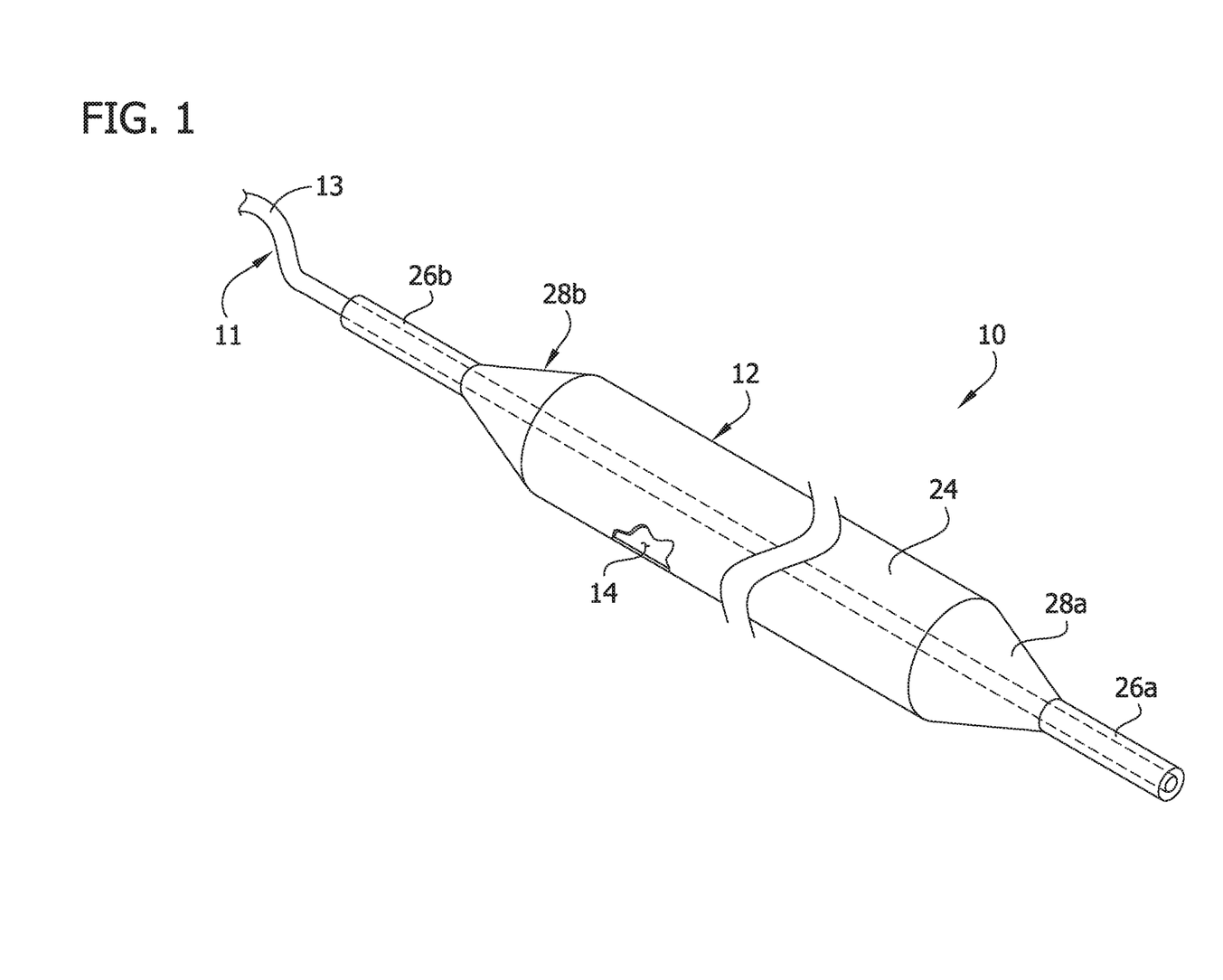
FIG. 1 is a fragmentary perspective of a balloon catheter including a medical balloon.

Referring to FIG. 1, one embodiment of a balloon catheter is generally indicated at reference number 10. The balloon catheter 10 includes a catheter, generally indicated at 11, and a medical balloon, generally indicated at 12, that is secured to the catheter 11 as explained below. The catheter 11 has a catheter body 13 that extends axially through an interior chamber 14 of the balloon 12 to form the balloon catheter 10. The catheter 11 is suitably configured to selectively deliver fluid to the interior chamber 14 of the balloon 12 to expand an outer circumference (i.e., an outer periphery) of the balloon. The balloon 12 is shown in its expanded or inflated configuration throughout the drawings, with the understanding that in its uninflated and deflated configurations, the balloon is capable of folding lengthwise such that the outer circumference of the balloon in its uninflated and deflated configurations is smaller than in its expanded or inflated configuration. The balloon 12 and the catheter body 13 have suitable shapes and dimensions for introduction into a desired body lumen for treatment therein. Typically, the balloon 12, in its uninflated initial configuration, is introduced into the body lumen using an introducer sheath (not shown). The uninflated balloon 12 is delivered to a treatment location within a body lumen (e.g., a blood vessel) by tracking through the introducer sheath and ultimately exiting a distal end of the sheath to reach the treatment location. Once the uninflated balloon 12 has reached the treatment location, fluid is delivered into the balloon, thereby expanding the outer circumference of the balloon (i.e., balloon is inflated). After treatment, the balloon 12 is deflated and "pulled back" into the introducer sheath. The balloon catheter 10 can then be withdrawn from the introducer sheath and the patient's body. It may be necessary or desired to re-introduce the balloon catheter 10 into a body lumen, through the introducer sheath, to further treat the body lumen.

The illustrated balloon catheter 10 may be configured for introduction along and inflation (i.e., circumferential or peripheral expansion) within a blood vessel for treating vascular stenosis. As an example, the medical balloon 12 of the illustrated balloon catheter 10 may be configured for introduction along and inflation within one or more of peripheral arteries and veins, coronary arteries and veins, renal arteries and veins, cerebral arteries and veins, and carotid arteries. In other examples, the medical balloon 12 may be configured for introduction along and inflation within other body lumens for treating stenosis of those lumens. The balloon 12 may be configured for treating other body lumens and/or for other treatments of those lumens.

Figure 2:
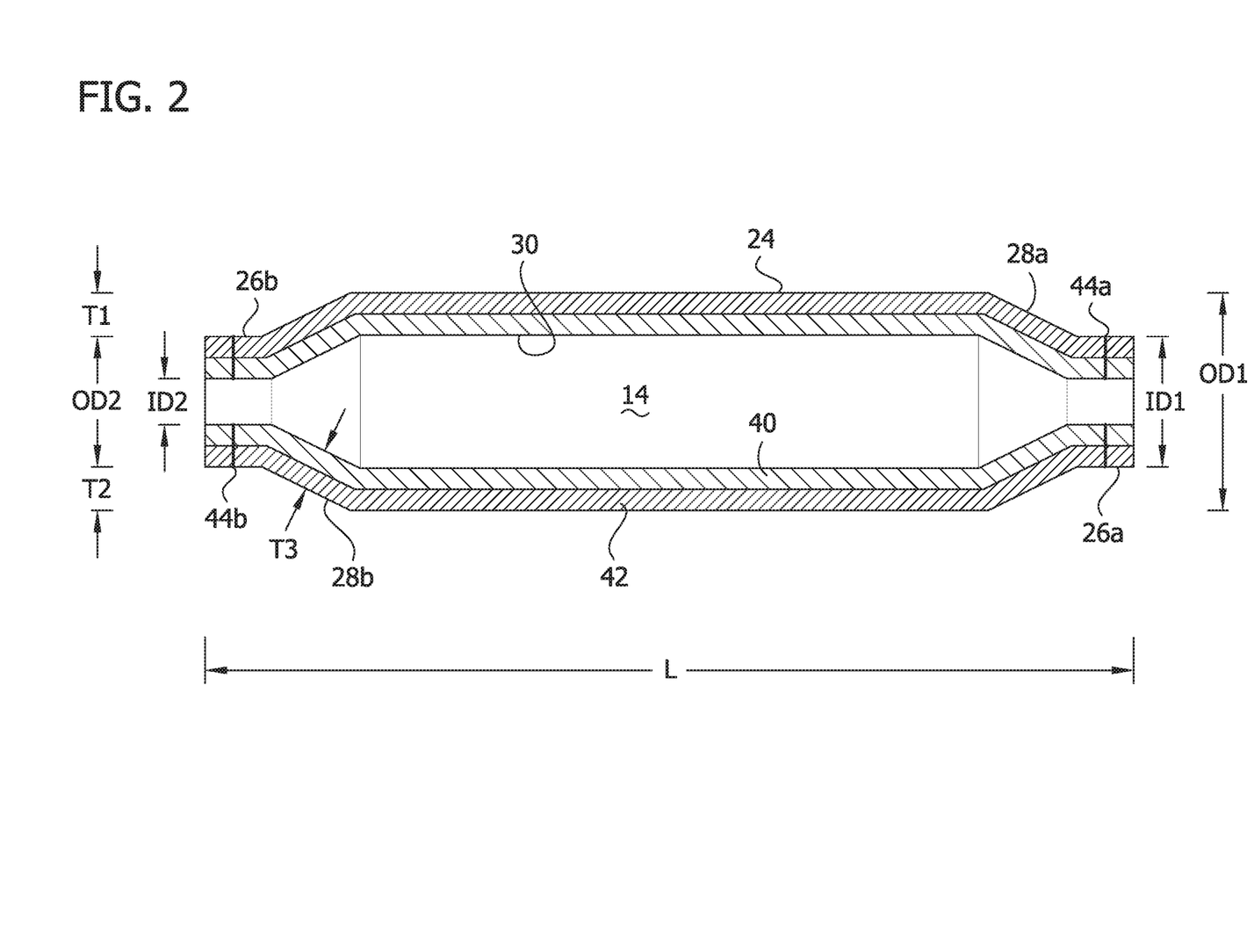
FIG. 2 is a longitudinal cross section of a balloon of the balloon catheter schematically illustrating the structural layers of the balloon.

Referring to FIG. 2, the medical balloon 12 has a length L. The length L of the balloon 12 may measure from about 10 mm to about 300 mm, in one example. The balloon 12 comprises a balloon body section 24; opposite proximal and distal waist sections 26a, 26b, respectively, at opposite longitudinal ends of the balloon; and opposite proximal and distal cone sections 28a, 28b, respectively, at corresponding proximal and distal ends of the body section intermediate the body section and the corresponding proximal and distal waist sections. The body section 24 interconnects and is disposed between the distal and proximal cone sections 28a, 28b. It is understood that the balloon 12 may have other sections, structures, and/or components without departing from the scope of the present invention.

In the illustrated embodiment, the body section 24 is generally tubular, defining a portion of the interior chamber 14 for receiving fluid to expand an outer circumference (i.e., an outer dimension) of the body section. The body section 24 has an expanded inner diameter ID1 (i.e., an inner cross-sectional dimension) defined by an interior surface 30 of the balloon 12, an expanded outer diameter OD1, and a single-wall thickness T1 that may be generally uniform along the length of the body section. In one example, the expanded outer diameter OD1 may measure greater than about 3 mm, and in one example, from about 3 mm to about 30 mm, the single-wall thickness T1 may measure from about 0.0005 in (0.0127 mm) to about 0.003 in (0.0762 mm). The body section 24 may have other shapes and dimensions without departing from the scope of the present invention.

The distal and proximal waist sections 26a, 26b are generally tubular and, in the illustrated embodiment, are configured to receive the catheter body 13 therein. Each waist section 26a, 26b has an outer diameter OD2 less than the outer diameter OD1 of the body section 24. Single-wall thicknesses T2 of the waist sections 26a, 26b may be greater than the single-wall thickness T1 of the body section 24. It is understood that the waist sections 26a, 26b may be omitted from the balloon 12 without departing from the scope of the present invention.

In general, the distal and proximal cone sections 28a, 28b are mirror images of one another. Each cone section 28a, 28b has respective inner and outer ends and a length extending between the inner and outer ends. An exterior surface of each cone section 28a, 28b has a generally conical (e.g., frustoconical) shape and a circumference or periphery (i.e., an outer dimension) and an outer diameter (i.e., an outer cross-sectional dimension) tapering outwardly toward the outer end of the respective cone section. An interior surface of the cone section 28a, 28b also has a generally conical shape defining an inner circumference or periphery (i.e., an inner dimension) and an inner diameter (i.e., an inner cross-sectional dimension) of the cone section that tapers proximally toward its outer end. A single-wall thickness T3 of each cone section 28a, 28b may taper as the cone section extends from the outboard end toward the inboard end.

The illustrated balloon 12 is a multilayer balloon, comprising a first, inner structural layer 40 and a second, outer structural layer 42. As explained below, embodiments of balloons having n layers, where n is greater than or equal to two, are expressly contemplated. Thus, balloons with more than two structural layers are also possible. As used herein, a "structural layer" is a circumferential layer of polymeric material that gives the balloon its structure and mechanical properties. The balloon may also include other, non-structural "layers," which are not considered "structural layers." For example, a lubricant coating or layer (not shown) may be applied to the outermost structural layer (i.e., the exterior of the balloon), but the lubricant coating is not considered a structural layer if its sole function is to provide lubricity to the balloon. Moreover, the balloon 12 may include a non-structural layer defining the interior surface of the balloon that is not a structural layer and/or the balloon may include one or more non-structural layers that are radially between (i.e., sandwiched between) adjacent structural layers.

It will be understood that the terms "inner" and "outer" are used in a radially relative sense when describing the structural layers of a balloon in this disclosure. A layer (e.g., the first layer 40) can be an "inner" layer if it is positioned radially inward of another, "outer" layer (e.g., the second structural layer 42), even if the inner layer is not the innermost layer. Likewise, a layer (e.g., the second layer 42) can be an "outer" layer if it is positioned radially outward of another, "inner" layer (e.g., the first structural layer 40) even if the outer layer is not the outermost layer. Of course, the inner and outer layers can also be the innermost and outermost layers, respectively, as shown in FIG. 2.

In the illustrated embodiment, each of the structural layers 40, 42 extends the entire length L of the balloon 12. In other embodiments, one or more structural layers can extend less than the entire length of the balloon (e.g., along only the balloon body section, along the balloon body and cone sections, along only a portion of the balloon body section, etc.). Each of the structural layers 40, 42 includes respective proximal and distal waist section, proximal and distal cone sections, and a balloon body section at the respective sections of the balloon 12. The waist sections of the inner structural layer 40 are concentrically received in the waist sections of the outer structural layer 42; the cone sections of the inner structural layer 40 are concentrically received in the cone sections of the outer structural layer 42; and the balloon body section of the inner structural layer 40 is concentrically received in the balloon body section of the outer structural layer 42. In one or more embodiments, the outer surface of the inner structural layer 40 directly engages the inner surface of the outer structural layer 42 without an intermediate non-structural material such as a lubricant or other slip agent. As will be explained in further detail below, in one or more embodiments the structural layers 40, 42 may include materials that minimize the amount of friction between the structural layers to promote substantially free sliding of the layers relative to one another.

In one or more embodiments, the inner structural layer 40 is suitably secured to the outer structural layer 42 only at one or both of the waist section 26a, 26b of the balloon 12. For example, the inner structural 40 can be welded to the outer structural layer 42 along radial or circumferential welds 44a, 44b. Other ways of securing the inner structural layer 40 to the outer structural layer 42 (e.g., adhesives, fasteners, etc.) can also be used. The inner structural layer 40 and outer structural layer 42 are unsecured to one another between the distal and proximal welds 44a, 44b (e.g., between the distal and proximal waist sections 26a, 26b). That is, aside from the welds 44a, 44b at the waist sections 26a, 26b of the balloon 12, the only restraint against free sliding movement of one of the structural layers 42, 44 relative to the other structural layer is the frictional engagement of the two layers. Thus, the inner and outer structural layers 40, 42 are unsecured to one another at the distal and proximal cone sections 28a, 28b and the body section 24. As explained below, the structural layers 42, 44 are configured to minimize the friction between the layers so that the unsecured portions of the two layers are permitted to slide substantially freely relative to one another. It is believed that the substantially free sliding of the structural layers 42, 44 between the waist sections 26a, 26b of the balloon improves folding of the balloon 12.

To minimize the probability of pinhole leaks adversely affecting the balloon 12, the separate inner and outer structural layers 40, 42 provide separate fluid barriers. As will be explained in further detail below, the outer structural layer 42 of the illustrated balloon 12 acts as stress-bearing layer that substantially enhances the strength and decreases the compliance of the balloon, and the inner structural layer 40 has a substantially monolithic and uniform (e.g., non-reinforced) polymer film construction that acts as a fluid impermeable liner within the outer stress-bearing layer. The use of separate fluid barriers with different properties is believed to reduce the likelihood of rupture due to pinhole leaks while providing a suitable rated burst pressure for a non-compliant or semi-compliant balloon (e.g., at least about 40 atm for balloons having an outer diameter OD1 of from about 4 mm to about 20 mm and a length L of from about 20 mm to about 40 mm; at least about 35 atm for balloons having an outer diameter OD1 of from about 8 mm to about 10 mm and a length L of from about 60 mm to about 80 mm; and at least about 30 atm for balloons having an outer diameter OD1 of about 12 mm and a length L of from about 20 mm to about 40 mm).

As discussed above, the illustrated outer structural layer 42 is configured to be a stress-bearing layer (i.e., to bear a substantial portion of the stresses imparted on the balloon 12 in use without mechanical failure). To withstand substantial stresses, the outer structural layer 42 is configured to be a non-compliant or semi-compliant balloon layer having a high rated burst pressure. For example, if the inner structural layer 40 were removed from the balloon 12, the outer structural layer 42 would be capable of independently operating as a non-compliant or semi-compliant medical balloon having a rated burst pressure of, for example, at least about 40 atm for balloons having an outer diameter OD1 of from about 4 mm to about 20 mm and a length L of from about 20 mm to about 40 mm; at least about 35 atm for balloons having an outer diameter OD1 of from about 8 mm to about 10 mm and a length L of from about 60 mm to about 80 mm; and at least about 30 atm for balloons having an outer diameter OD1 of about 12 mm and a length L of from about 20 mm to about 40 mm. Thus, the outer structural layer 42 can, in one or more embodiments, comprise a non-compliant or semi-compliant medical balloon.

Figure 2A:
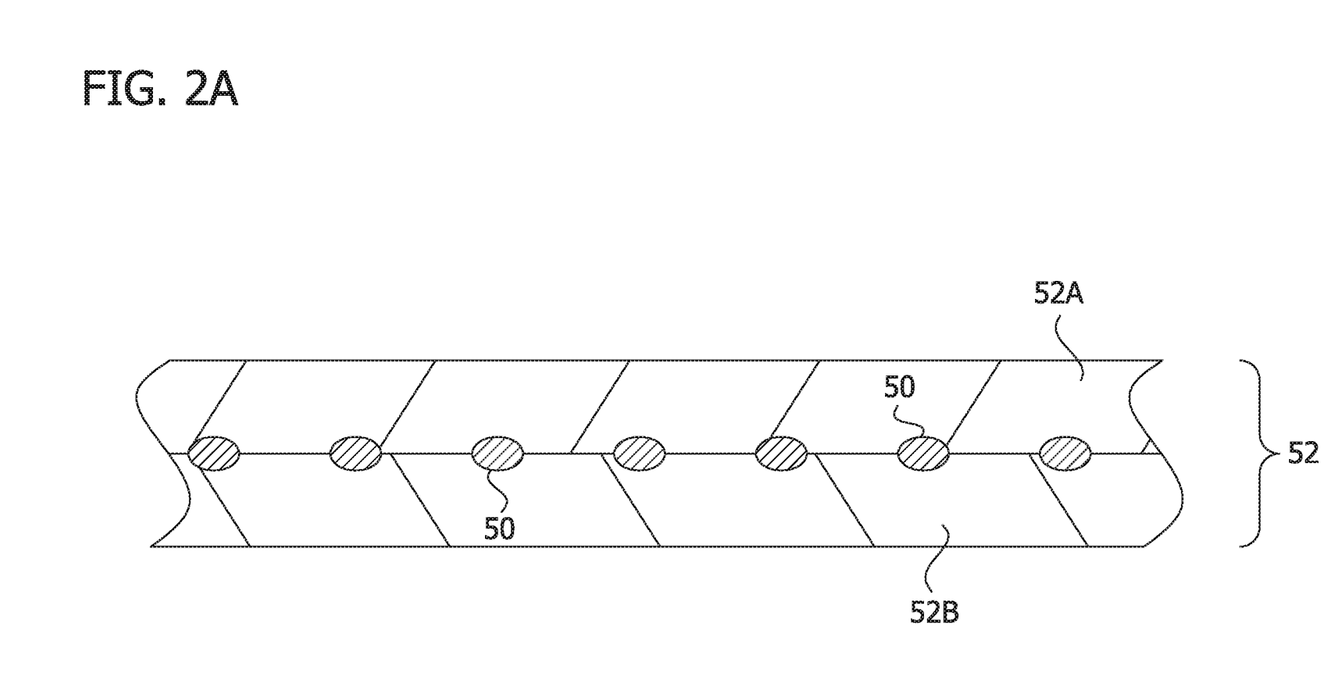
FIG. 2A is an enlarged fragmentary schematic cross section of a fiber-reinforced polymer for forming a structural layer of the balloon.

In one or more embodiments, the outer structural layer 42 can comprise a fiber-reinforced polymer balloon, such as a polymer fiber braided (PFB) balloon as is known in the art. For example, as shown in FIG. 2A, the outer structural layer 42 suitably comprises reinforcing fibers 50, such as PEEK fibers, carbon fibers, glass fibers, aramid fibers, etc., that are stabilized together to form a fibrous fabric and suspended within a polymer matrix 52. For example, the fibers 50 can be woven, braided, felted, matted, stitched, etc. to form a stabilized fiber fabric. Alternatively, the fibers 50 can be loose fibers suspended in the polymer matrix and thereby be individually stabilized within the polymer matrix. In the illustrated embodiment, the polymer matrix 52 comprises opposing polymer sublayers 52A, 52B that are covalently bonded together with the fibers 50 sandwiched therebetween to form the composite outer structural layer 42. The fibers 50 can also be suspended in a polymer matrix in other ways, such as by curing a liquid polymer in which the reinforcing fibers are suspended. The polymer matrix 52 that supports the reinforcing fibers 50 can suitably comprise a nylon (e.g., nylon 11, nylon 12, etc.) or a Polyether Block Amide (PEBA) (Pebax 72D, Pebax 74D, sold by Arkema of Paris, France). Other materials and constructions can also be used to form the non-compliant or semi-compliant outer structural layer 42 in other embodiments.

In one or more embodiments, inner structural layer 40 may comprise a non-reinforced balloon layer, such as a polymeric balloon layer that is free from reinforcing fibers and other reinforcing additives. Certain exemplary materials include a PEBA copolymer (e.g., Pebax 72D, Pebax 74D, sold by Arkema of Paris, France), a nylon 12, a nylon 11, blends thereof, etc. The inner structural layer 40 may have a lower shore hardness than the outer structural layer 42. The inner structural layer 40 may have a balloon compliance of from about 0% to about 10%, or more preferably from about 4% to about 7%. The inner structural layer 40 may be more compliant than the outer structural layer 42. The inner structural layer 40 may have a tensile elongation at break that is significantly higher (e.g., on the order of about 350% higher or more) than the outer structural layer 42. It is believed that using an inner structural layer 40 that is more elastic than the outer structural layer 42 enhances the foldability of the balloon 12. In one or more embodiments, the foldability of the balloon 12 is such that balloons having the length L1 and outer diameter OD1 are compatible with a predetermined sheath size. For example, in certain embodiments, balloons 12 having an outer diameters OD1 ranging from about 4 mm to about 8 mm and lengths L1 ranging from about 20 mm to about 100 mm are compatible with 6 Fr sheaths; balloons 12 having an outer diameters OD1 ranging from about 9 mm to about 10 mm and lengths L1 ranging from about 20 mm to about 80 mm are compatible with 7 Fr sheaths; and balloons 12 having an outer diameters OD1 of about 12 mm and lengths L1 ranging from about 20 mm to about 40 mm are compatible with 8 Fr sheaths.

The more elastic inner structural layer 40 also acts as a liner or internal barrier against pinhole leaks that may form in the outer structural layer 42 due to the presence of reinforcing fibers, etc. In general, the non-reinforcing inner structural layer 40 would be expected to have a lower independently rated burst pressure than the outer structural layer 42. But since the inner structural layer 40 is received in the outer structural layer 42, during expansion of the balloon 12, the outer structural layers bears the majority of the forces imparted on the balloon. The stresses imparted on the inner structural layer 40 are thereby minimized as the outer structural layer 42 bears the stresses generated by the inflation fluids in the chamber 14 that press the inner structural layer tightly against the outer structural layer. The non-reinforced inner structural layer 40 may be less likely to rupture due to pinhole leaks therein than the outer structural layer because pinhole leaks are thought to be less likely to form in the inner structural layer than the outer structural layer. And furthermore, the inner structural layer 40 is prevented from rupturing due to internal fluid pressures that exceed the independent rated burst pressure because the outer structural layer 42 bears the majority of the forces imparted on the balloon 12 during expansion.

As described above, the inner and outer structural layers 40, 42 are configured to slide relative to one another at one or both of the body section 24 and the cone sections 28a, 28b. It is believed that this construction provides stress distribution between the inner and outer structural layers 40, 42. Although, slip agents such as lubricants can be provided between the two layers 40, 42 to promote sliding, it can be difficult to ensure even distribution of the slip agent along the length L and around the circumference of the interface between the layers during use. In one or more embodiments, no slip agent is used and the inner and outer structural layers 40, 42 comprise polymers of different types that have a low coefficient of friction between them. For example, as explained above, it is contemplated that either of the structural layers 40, 42 can comprise a PEBA or a nylon. In one or more suitable embodiments, one of the structural layers 40, 42 comprises a PEBA and the adjacent structural layer comprises a nylon arranged to form a PEBA-nylon interface between the two structural layers. The use of dissimilar polymers decreases the coefficient of friction between the two structural layers 40, 42 as compared with multilayer balloon constructions that use, for example, two structural layers comprising a PEBA and forming a PEBA-PEBA interface. Moreover, it is believed that using adjacent structural layers of a PEBA and a nylon creates a sufficiently low coefficient of friction between the layers 40, 42 to allow them to slide relative to one another during use without the use of an intermediate slip agent and without creating localized stress points in the non-reinforced inner structural layer that could cause it to rupture. Inner and outer structural layers 40, 42 that each comprises a nylon would also have a low coefficient of friction therebetween and are also possible in certain embodiments. But forming the multilayer balloon 12 to form a PEBA-nylon interface between the structural layers 40, 42 is thought to enhance the sheathing characteristics of the balloon 12 as compared with a balloon having a nylon-nylon interface by strengthening the layer interaction when the balloon is deflated. Thus, in suitable embodiments of a balloon having n structural layers, at each interface of two adjacent structural layers, one structural layer may comprise a first polymer and the other structural layer may comprise a second polymer of a different type to form an interface of polymers of different types between the structural layers (e.g., by using radially successive structural layers alternating between one of a PEBA and a nylon to form one or more PEBA-nylon interfaces between the n structural layers).

Figure 3:
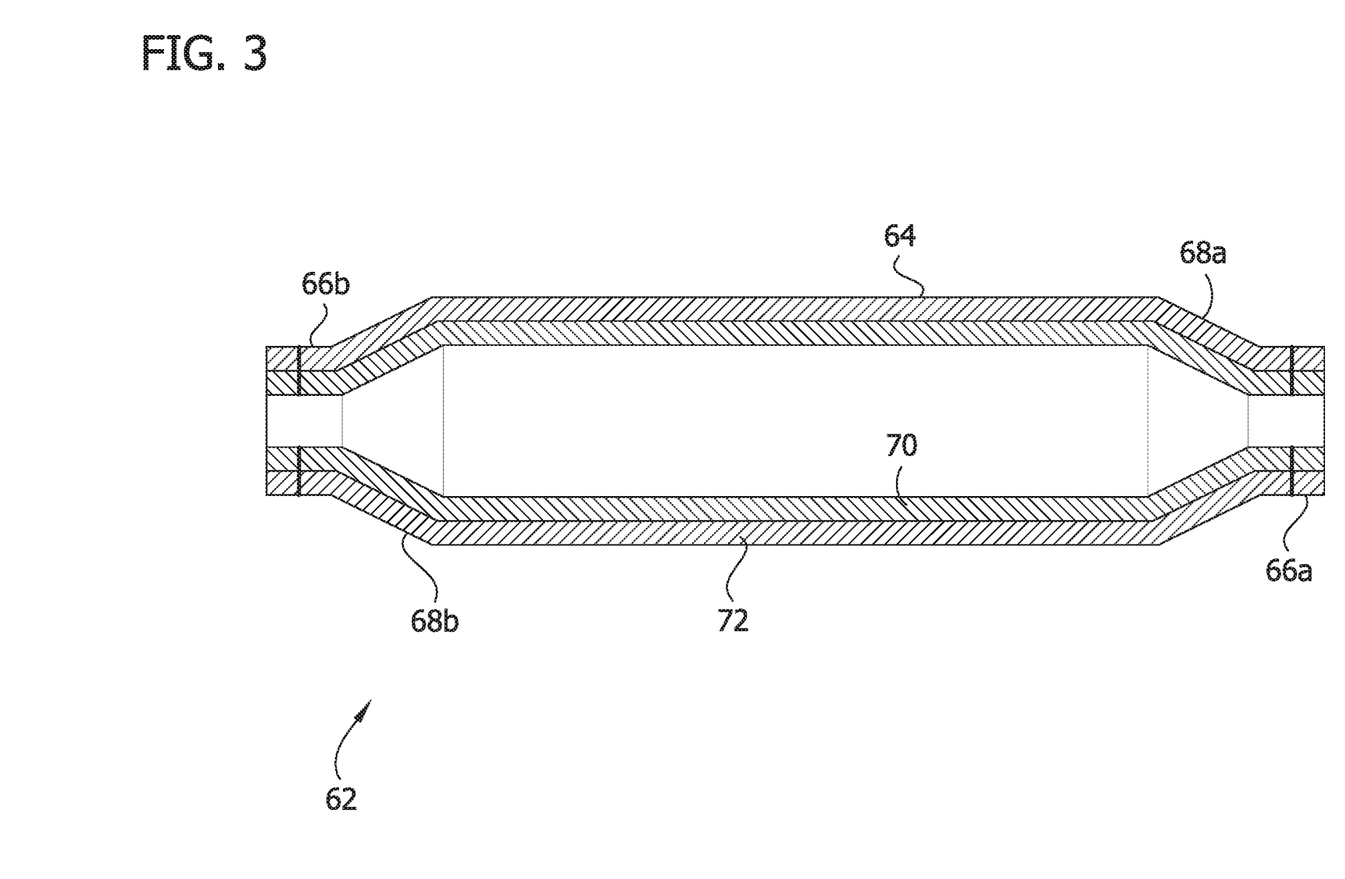
FIG. 3 is a longitudinal cross section of another embodiment of a balloon schematically illustrating the structural layers of the balloon.

Referring to FIG. 3, another embodiment of a multilayer medical balloon that is suitable for use in a balloon catheter (e.g., by being operatively positioned the catheter 11 as set forth above for the balloon 12) is generally indicated at 62. Like the balloon 12, the balloon 62 has a tubular balloon body section 64, distal and proximal waist sections 66a, 66b, and distal and proximal cone sections 68a, 68b. The balloon 62 is also a bilayer balloon like the balloon 12, comprising an inner structural layer 70 and a concentric outer structural layer 72. The inner structural layer 70 is attached to the outer structural layer at the waist sections 66a, 66b of the balloon 62 but is substantially free to slide relative to the outer structural layer along the cone sections 68a, 68b and balloon body section 64. Like the outer structural layer 42 of the balloon 12, the outer structural layer 72 comprises a fiber-reinforced polymer. But unlike the inner structural layer 40, the inner structural layer 70 of the balloon 62 also comprises a fiber reinforced polymer. As described above, the structural layers 70, 72 suitably comprise different types of polymers to minimize the coefficient of friction between the layers. Furthermore, as above, it is desirable to construct the inner structural layer 70 to have a higher tensile elongation at break point than the outer structural layer 72. As compared with the balloon 12, the balloon 62 is thought to have a higher rated burst pressure but lower foldability, requiring larger sheaths for balloons of the same size.

Figure 4:
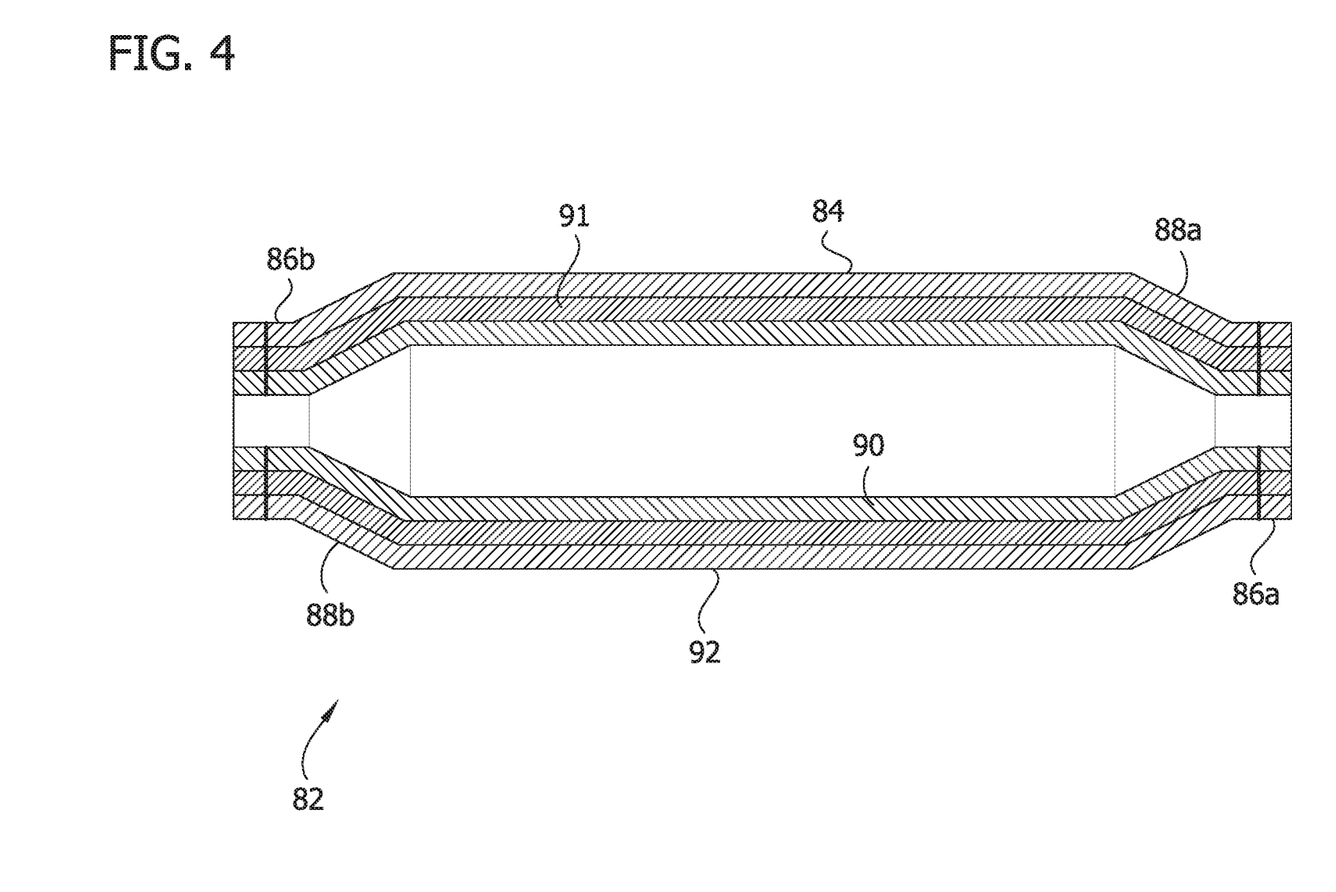
FIG. 4 is a longitudinal cross section of another embodiment of a balloon schematically illustrating the structural layers of the balloon.

Referring to FIG. 4, another embodiment of a multilayer medical balloon that is suitable for use in a balloon catheter (e.g., by being operatively positioned the catheter 11 as set forth above for the balloon 12) is generally indicated at 82. Like the balloon 12, the balloon 82 has a tubular balloon body section 84, distal and proximal waist sections 86a, 86b, and distal and proximal cone sections 88a, 88b. Unlike the balloon 12, the balloon 82 is a tri-layer balloon, comprising an inner structural layer 90, a concentric intermediate structural layer 91, and a concentric outer structural layer 92. In the illustrated embodiment, the intermediate structural layer 91 comprises a fiber reinforced balloon layer and each of the inner and outer structural layers 90, 92 comprises a non-reinforced balloon layer that is free from reinforcing fibers and other reinforcing additives. In this embodiment, the intermediate layer 91 acts as a stress-bearing layer and the inner and outer structural layers 90, 92 are believed to act as an envelope or inner and outer barriers against pinhole leaks formed in the stress bearing intermediate layer. Suitably, adjacent ones of the structural layers 90, 92 comprise different materials to promote sliding among the layers. For example, in one embodiment, each of the inner and outer layers 90, 92 comprises a PEBA and the intermediate layer 91 comprises nylon. In another embodiment, each of the inner and outer layers 90, 92 comprises nylon and the intermediate layer 91 comprises a PEBA.

As discussed above, in one or more embodiments, a fiber-reinforced balloon layer (e.g., the intermediate layer 91) may be formed by sandwiching reinforcing fibers 56 between two opposing sheets of polymer film 52A, 52B. It is contemplated that in one or more embodiments, the intermediate structural layer 91 is formed by sandwiching the reinforcing fibers between opposing film layers comprising different types of polymers, such as one film layer 52A of a PEBA and the other film layer 52B of nylon. When the intermediate structural layer 91 has this construction, the inner and outer structural layers 90, 92 suitably comprise different materials. For example, when the intermediate structural layer 91 is constructed of an inner film sheet 52B comprising a nylon and an outer film sheet 52A comprising a PEBA, the inner structural layer 90 can suitably comprise a PEBA and the outer structural layer 92 can suitably comprise a nylon. Likewise, when the intermediate structural layer 91 is constructed of an inner film sheet 52B comprising a PEBA and an outer film sheet 52A comprising a nylon, the inner structural layer 90 can suitably comprise a nylon and the outer structural layer 92 can suitably comprise a PEBA.

Figure 5:
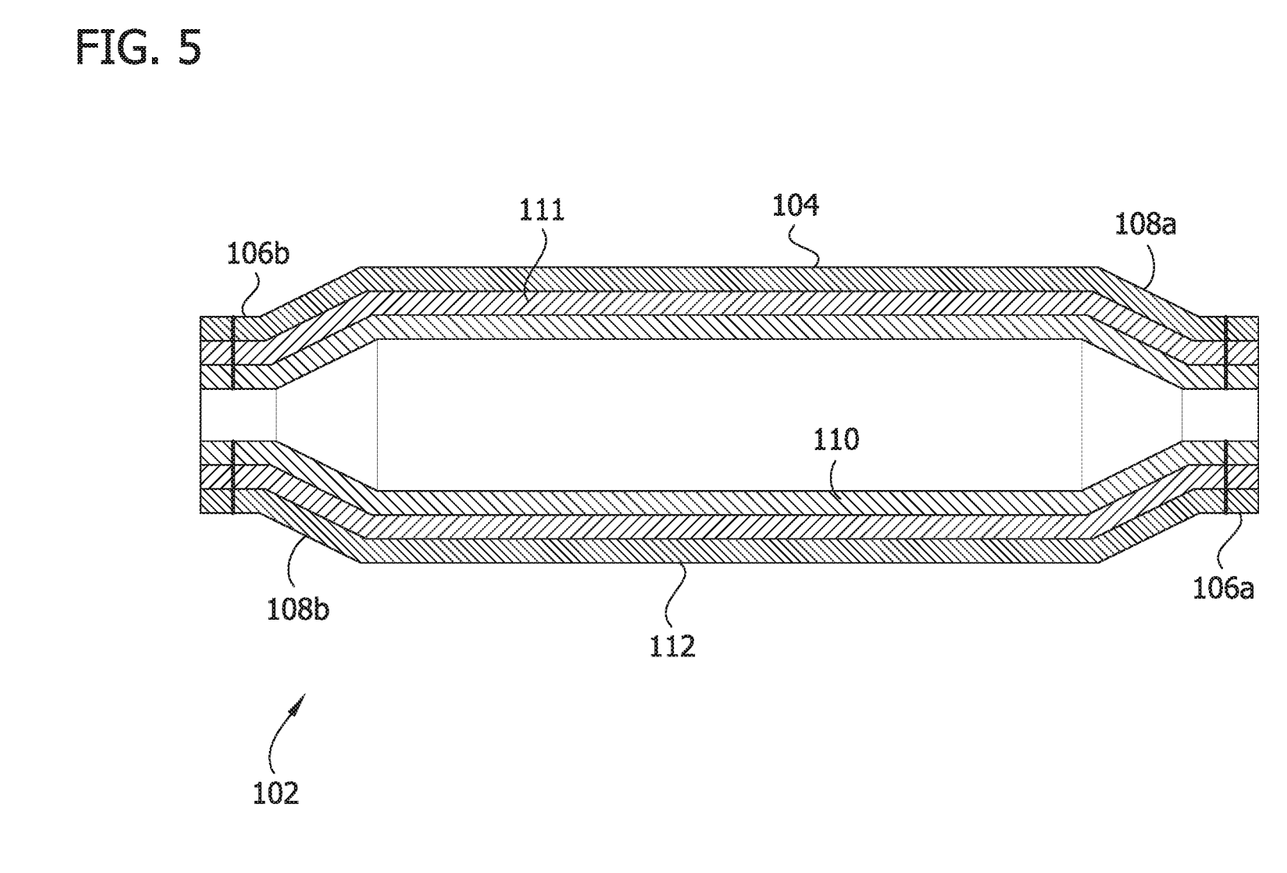
FIG. 5 is a longitudinal cross section of another embodiment of a balloon schematically illustrating the structural layers of the balloon.

Referring to FIG. 5, another embodiment of a multilayer medical balloon that is suitable for use in a balloon catheter is generally indicated at 102. Like the balloon 12, the balloon 102 has a tubular balloon body section 104, distal and proximal waist sections 106a, 106b, and distal and proximal cone sections 108a, 108b. Like the balloon 82, the balloon 102 is a tri-layer balloon, comprising an inner structural layer 110, a concentric intermediate structural layer 111, and a concentric outer structural layer 112. Unlike the balloon 82, however, the outer structural layer 112 comprises a fiber-reinforced balloon layer and the inner and intermediate structural layers 110, 111 comprise non-reinforced balloon layers that are free from reinforcing fibers and other reinforcing additives. The inner structural layer 110 may have a shore hardness that is less than the shore hardness of the intermediate structural layer 111, and the shore hardness of the intermediate structural layer may be less than the outer structural layer 112. For example, the inner structural layer 110 can comprise Pebax 72D and the intermediate structural layer can comprise Pebax 74D, which has a greater shore hardness than Pebax 72D. In other embodiments, the structural layers 110, 111, 112 are configured so that the interfaces between adjacent layers are formed by surfaces comprising dissimilar materials. For example, the inner structural layer 110 can comprise a PEBA, the intermediate structural layer 111 can comprise a nylon, and the outer structural layer 112 can comprise a PEBA (e.g., an inner sheet of film 52B forming the outer structural layer 112 can comprise a PEBA). Still other material combinations are also possible.

Figure 6:
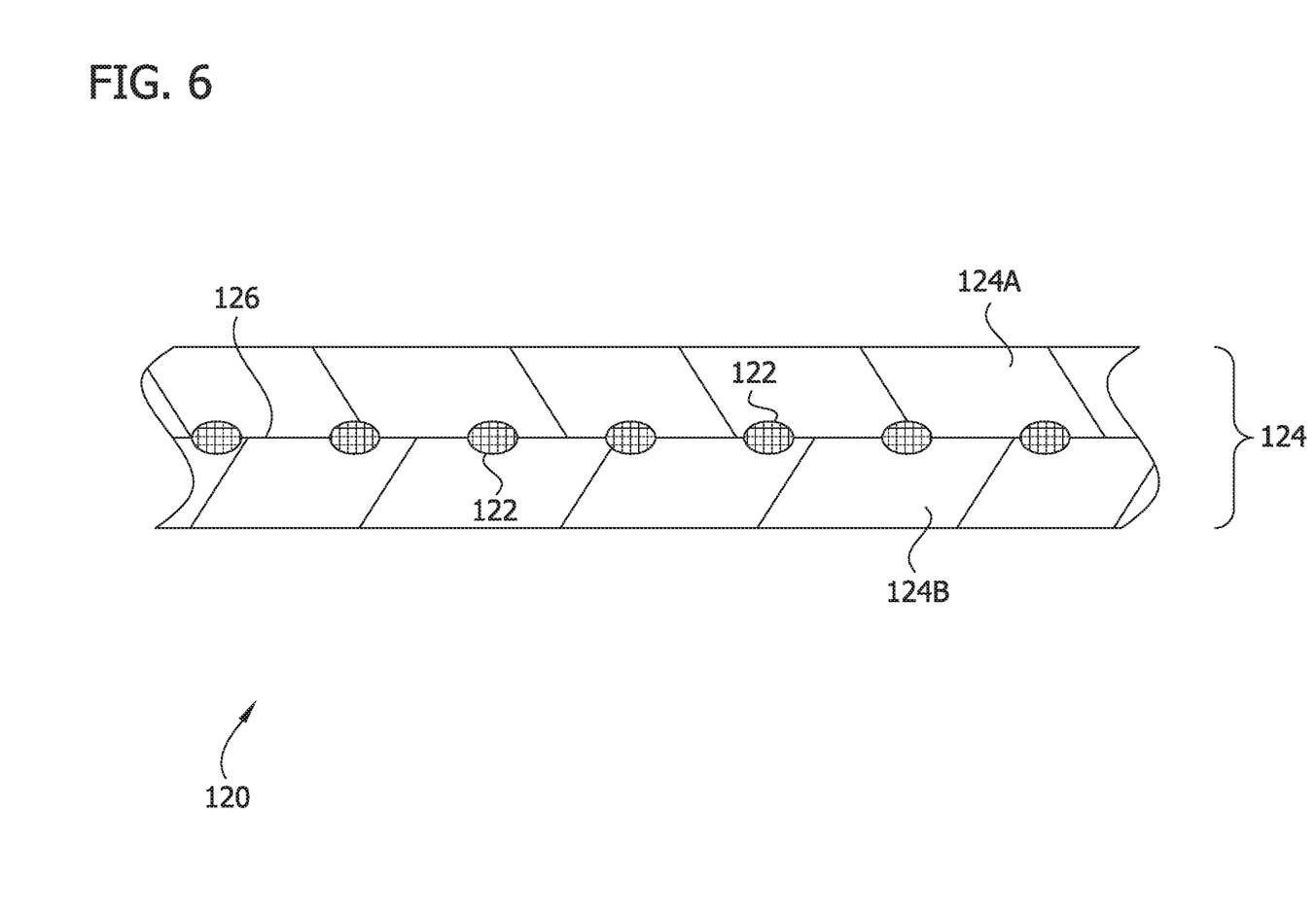
FIG. 6 is an enlarged fragmentary schematic cross section of a metal fiber-reinforced polymer material for forming a structural layer of a balloon.

Referring to FIG. 6, in one or more embodiments, a suitable material for a stress-bearing structural layer (e.g., any of the structural layers 42, 70, 72, 91, 112, etc.) comprises a metal-polymer composite, generally indicated at 120. For example, instead of using the fibers 50 in a fiber-reinforced structural layer as discussed above, a structural layer can comprise a mesh or open fabric of braided, woven or otherwise stabilized metal fibers 122. Exemplary metal fibers 122 for use in the outer structural layer 120 include those comprising nitinol, MP35N, stainless steel, etc. As shown in FIG. 6, the metal fibers 122 can suitably be suspended in a polymer matrix 124. For example, the metal fibers 122 can be sandwiched between an outer polymer sublayer 124A and an inner polymer sublayer 124B. Suitably, the polymer sublayers 124A, 124B are covalently bonded at central seam 126 and are covalently bonded to the metal fibers 122. Alternatively, the polymer layers 124A, 124B can be physically bonded to the metal fibers 122, instead of being covalently bonded. In one or more embodiments, a surface treatment can be applied to the metal fibers 122 to promote affinity with the polymer layers 124A, 124B. In certain embodiments, the material illustrated in FIG. 6 and described in this paragraph can be used to form a single-layer balloon. In other embodiments, the material is used to form a stress bearing layer in a multilayered balloon (e.g., any of the structural layers 42, 70, 72, 91, 112, etc.).

In another embodiment, a medical balloon comprises a structural layer formed of a fiber reinforced polymer comprising both metal reinforcing fibers and polymer reinforcing fibers. For example, metal and polymer reinforcing fibers can be woven or otherwise stabilized together to from a sheet of reinforcing fibers of different types, or the metal and polymer fibers could form separate sheets of reinforcing fibers (i.e., a metal reinforcing fiber sheet and a polymer reinforcing fiber sheet) that are encapsulated together within a polymer matrix to form a structural layer. In still other embodiments, a structural layer can comprise loose metal fibers and/or loose polymer fibers.

In any of the above-described embodiments, one or more layers of the balloon (e.g., the outer layer) may be suitable for being coated with a drug to deliver the drug to the target site. In one or more embodiments, the one or more layers of the balloon are coated with a drug. In one or more examples, a suitable drug for the drug-coated balloon includes paclitaxel and/or other drugs that are suitable as an anti-proliferative agent to inhibit or decrease stenosis, including restenosis, of a treat body lumen. Other types of anti-proliferative drugs may be used, and other types of drugs for treatment may be used.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A medical balloon comprising:
an inner structural layer;
an intermediate structural layer disposed radially outward of the inner structural layer; and
an outer structural layer disposed radially outward of the intermediate structural layer,
wherein the intermediate structural layer comprises an inner portion defining an inner surface of the intermediate structural layer adjacent the inner structural layer and an outer portion defining an outer surface of the intermediate structural layer adjacent the outer structural layer,
wherein the inner portion is formed from a first material and the outer portion is formed from a second material different than the first material such that the inner and outer surfaces of the intermediate structural layer are formed by different materials,
wherein the intermediate structural layer further comprises reinforcing fibers sandwiched between the inner portion and the outer portion, each of the reinforcing fibers having a cross-sectional perimeter,
wherein each of the first and second materials partially surrounds the cross-sectional perimeter of each of the reinforcing fibers such that together the first and second materials surround the cross-sectional perimeter of each of the reinforcing fibers.

2. The medical balloon as set forth in claim 1, wherein each of the inner portion and the outer portion comprises a respective film layer formed from the corresponding first and second materials.

3. The medical balloon as set forth in claim 1, wherein one of the inner portion and the outer portion comprises a polyether block amide film layer and the other of the inner portion and the outer portion comprises a nylon film layer.

4. The medical balloon as set forth in claim 3, wherein one of the inner structural layer and the outer structural layer comprises a polyether block amide film layer and the other of the inner structural layer and the outer structural layer comprises a nylon film layer.

5. The medical balloon as set forth in claim 1, wherein each of the inner portion and the outer structural layer comprises a polyether block amide film layer and each of the outer portion and the inner structural layer comprises a nylon film layer.

6. The medical balloon as set forth in claim 1, wherein each of the inner portion and the outer structural layer comprises a nylon film layer and each of the outer portion and the inner structural layer comprises a polyether block amide film layer.

7. The medical balloon as set forth in claim 1, wherein the inner structural layer has an interfacing surface that defines an inner interface with the inner surface of the intermediate structural layer, the interfacing surface being formed by a different material than the inner surface of the intermediate structural layer.

8. The medical balloon as set forth in claim 1, wherein the outer structural layer has an interfacing surface that defines an outer interface with the outer surface of the intermediate structural layer, the interfacing surface being formed by a different material than the outer surface of the intermediate structural layer.

9. The medical balloon as set forth in claim 1, wherein the inner structural layer and the outer structural layer are formed from different materials.

10. The medical balloon as set forth in claim 1, wherein each of the other two of the inner structural layer, the intermediate structural layer, and the outer structural layer comprises a non-reinforced polymer film.

11. The medical balloon as set forth in claim 1, wherein the fiber-reinforced polymer comprises metal reinforcing fibers in a polymer matrix.

12. The medical balloon as set forth in claim 1, wherein each of the inner portion and the outer structural layer comprises a polyether block amide film layer and each of the outer portion and the inner structural layer comprises a nylon film layer.

13. The medical balloon as set forth in claim 1, wherein each of the inner portion and the outer structural layer comprises a nylon film layer and each of the outer portion and the inner structural layer comprises a polyether block amide film layer.

14. The medical balloon as set forth in claim 1, wherein the reinforcing fibers are spaced apart from one another by gaps, wherein the inner and outer portions of the intermediate structural layer interface with one another in the gaps.

\* \* \* \* \*